(12) United States Patent
Bryan

(10) Patent No.: US 9,656,946 B2
(45) Date of Patent: May 23, 2017

(54) METHOD OF MAKING A TEMPLATING AGENT

(71) Applicant: JOHNSON MATTHEY PLC, London (GB)

(72) Inventor: Richard Charles Bryan, Lancaster (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 15/060,979

(22) Filed: Mar. 4, 2016

(65) Prior Publication Data
US 2016/0185709 A1 Jun. 30, 2016

Related U.S. Application Data

(62) Division of application No. 14/471,737, filed on Aug. 28, 2014, now Pat. No. 9,321,723.

(60) Provisional application No. 61/870,973, filed on Aug. 28, 2013.

(51) Int. Cl.
| | | |
|---|---|---|
| C07C 209/00 | (2006.01) | |
| C07C 68/06 | (2006.01) | |
| C07D 211/98 | (2006.01) | |
| C07D 211/14 | (2006.01) | |
| C07C 209/16 | (2006.01) | |

(52) U.S. Cl.
CPC ............ *C07C 209/00* (2013.01); *C07C 68/06* (2013.01); *C07C 209/16* (2013.01); *C07D 211/14* (2013.01); *C07D 211/98* (2013.01); *C07C 2103/74* (2013.01)

(58) Field of Classification Search
CPC .............................. C07C 69/96; C07C 209/00
USPC ........................................... 564/281; 558/260
See application file for complete search history.

(56) References Cited

U.S. PATENT DOCUMENTS 5,789,614 A * 8/1998 Yagii ..................... C07C 269/04
560/158

FOREIGN PATENT DOCUMENTS

| GB | 1587925 A | 4/1981 |
|---|---|---|
| WO | 9952368 A1 | 10/1999 |

OTHER PUBLICATIONS

Sima et al. "The syntheses of carbamates . . . " Tetrahedron Lett. v.43 p. 8145-8147 (2002).*
Distaso et al. "Group 3 metal . . . " Tetrahedron v. 60, p. 1531-1539 (2004).*

* cited by examiner

Primary Examiner — Celia Chang

(57) ABSTRACT

A method for preparing 1-adamantyltrimethylammonium methylcarbonate or N,N-dimethyl-3,5-dimethylpiperidinium methylcarbonate is disclosed. The method comprises reacting dimethyl carbonate and 3,5-dimethylpiperidine or a 1-adamantylamine compound and in the presence of water in a sealed vessel at a temperature of from 80 to 200° C. The 1-adamantylamine compound is 1-adamantylamine, 1-adamantylmethylamine, or mixtures thereof.

9 Claims, No Drawings

METHOD OF MAKING A TEMPLATING AGENT

CROSS-REFERENCE TO RELATED APPLICATIONS

This application is a divisional of U.S. patent application Ser. No. 14/471,737, filed Aug. 28, 2014, allowed on Dec. 18, 2015, and claims priority benefit of U.S. Provisional Patent Application No. 61/870,973, filed Aug. 28, 2013, the disclosures of which are incorporated herein by reference in their entireties for all purposes.

FIELD OF THE INVENTION

The invention relates to a method for preparing 1-adamantyltrimethyl-ammonium methylcarbonate and N,N-dimethyl-3,5-dimethylpiperidinium methylcarbonate.

BACKGROUND OF THE INVENTION

1-Adamantyltrimethylammonium hydroxide and N,N-dimethyl-3,5-dimethylpiperidinium methylcarbonate are useful as a templating agents in the production of zeolites. A standard route to prepare ammonium salts of organic amines, such as 1-adamantyltrimethylammonium hydroxide, includes an alkylation step in which the organic amine is reacted with an alkylating agent such as dialkyl sulfates or methyl iodide. For example, U.S. Pat. No. 8,252,943 discloses a process for preparing ammonium compounds by reacting compounds containing a double-bonded nitrogen atom with a dialkyl sulfate with participation of both alkyl groups of the dialkyl sulfate and, if appropriate, subjecting the resulting ionic compound containing sulfate anions to an anion exchange. Likewise, U.S. Pat. No. 8,163,951 teaches a process for preparing quaternary ammonium compounds, which comprises reacting compounds comprising an $sp^3$-hybridized nitrogen atom with a dialkyl sulfate or trialkyl phosphate and subjecting the resulting ammonium compound to an anion exchange. U.S. Pat. Appl. Pub. No. 2012/0010431 discloses a process for preparing 1-adamantyltrimethylammonium hydroxide that comprises reacting 1-adamantyldimethylamine with dimethyl sulfate to give 1-adamantyltrimethylammonium sulfate, which is then subjected to anion exchange with an ion exchanger loaded with OH ions. In addition, U.S. Pat. No. 4,859,442 describes at Example 1 the preparation of 1-adamantyltrimethylammonium hydroxide by alkylation of 1-adamantylamine with methyl iodide, followed by ion exchange of the iodide anions with an ion exchange resin. U.S. Pat. No. 5,645,812, likewise, teaches the preparation and use of a N,N-diethyl-3,5-dimethylpiperidinium hydroxide templating agent.

In addition, U.S. Pat. No. 6,784,307 teaches a method of preparing quaternary ammonium alkylcarbonates (such as quaternary ammonium methocarbonates), quaternary ammonium bicarbonates, and quaternary ammonium carbonates by reaction of the corresponding tertiary amines with a cyclic carbonate and methanol. Zhuoqun Zheng et al. in Adv. Synth. Catal. 2007, 349, 1095-1101 and Chinese Pat. Appl. No. CN1948268 describe a process for preparing quaternary salts from amine salts and dimethyl carbonate in the presence of ethyl methyl imidizolium salts as catalysts. The same authors describe the quaternization of amine salts without a catalyst in Chinese Pat. No. CN101245019.

As with any chemical process, it is desirable to attain still further improvements in processes for preparing 1-adamantyltrimethyl-ammonium methylcarbonate and 1-adamantyl-trimethyl-ammonium hydroxide. We have discovered a new method to produce 1-adamantyltrimethyl-ammonium methylcarbonate with a high yield.

SUMMARY OF THE INVENTION

The invention is a method for preparing 1-adamantyltrimethylammonium methylcarbonate or N,N-dimethyl-3,5-dimethylpiperidinium methylcarbonate. The method comprises reacting dimethyl carbonate and a 1-adamantylamine compound or 3,5-dimethylpiperidine in the presence of water in a sealed vessel at a temperature of from 80 to 200° C. The 1-adamantylamine compound is 1-adamantylamine, 1-adamantylmethylamine, or mixtures thereof.

DETAILED DESCRIPTION OF THE INVENTION

The method of the invention comprises reacting dimethyl carbonate and a 1-adamantylamine compound or 3,5-dimethylpiperidine in the presence of water in a sealed vessel at a temperature of from 80 to 200° C.

The 1-adamantylamine compound or 3,5-dimethylpiperidine is reacted with dimethyl carbonate to produce 1-adamantyltrimethylammonium methylcarbonate or N,N-dimethyl-3,5-dimethylpiperidinium methylcarbonate in a combined methylation/quaternization step. The 1-adamantylamine compound is 1-adamantylamine, 1-adamantylmethylamine, or mixtures thereof.

Preferably, the reaction of 1-adamantylamine, 1-adamanylmethylamine or 3,5-dimethylpiperidine with dimethyl carbonate in the presence of water is performed at elevated temperature and pressure, for example in an autoclave. In addition to dimethyl carbonate, the 1-adamantylamine compound or 3,5-dimethylpiperidine, and water, the reaction may be performed in the presence of other solvents such as methanol or other aprotic solvents inert to the reaction conditions, but additional solvents are not required. Preferably, the reaction step involves mixing the 1-adamantylamine compound or 3,5-dimethylpiperidine with water, followed by the addition of dimethyl carbonate.

Typically, the reaction mixture containing 3,5-dimethylpiperidine or the 1-adamantylamine compound, water and dimethyl carbonate is heated at a temperature of about 80° C. to about 200° C. for a period greater than about 0.25 hours (preferably less than about 48 hours) in a sealed vessel under autogenous pressure. Alternately, the vessel may be fitted with a device to limit the rise in pressure by venting some of the carbon dioxide produced. More preferably, the reaction mixture is heated at a temperature range from about 100° C. to about 175° C., most preferably from about 120° C. to about 160° C. The reaction temperature may also be increased over the course of the reaction. The reaction is preferably performed from 1 to 24 hours. The reaction may be carried out in a batch, continuous, or semi-continuous manner using any appropriate type of reaction vessel or apparatus such as a stirred vessel or CSTR reactor.

Preferably, the molar ratio of dimethyl carbonate: 1-adamantylamine compound or 3,5-dimethylpiperidine is in the range of 5 to 20, more preferably the molar ratio is in the range of 8 to 14.

The presence of water is required for the methylation/quaternization reaction to occur. Preferably, the molar ratio of water:the 1-adamantylamine compound or 3,5-dimethylpiperidine is in the range of 1 to 4.

After the reaction is complete, the 1-adamantyltrimethylammonium methylcarbonate or N,N-dimethyl-3,5-dimethylpiperidinium methylcarbonate is preferably recovered. Suitable recovery methods include filtration and washing, rotary evaporation, centrifugation, and the like. In a preferred embodiment, the reaction mixture is cooled to ambient temperature and a portion of the reaction mixture (preferably reducing the reaction volume by greater than 25%) is stripped to remove any methanol that might have formed. The remaining slurry may be further cooled to a temperature less than 10° C., and the 1-adamantyltrimethylammonium methylcarbonate or N,N-dimethyl-3,5-dimethylpiperidinium methylcarbonate product isolated by filtration and then washed with cold dimethyl carbonate or acetone. The white crystalline product can be further dried under vacuum to produce the final 1-adamantyltrimethylammonium methylcarbonate or N,N-dimethyl-3,5-dimethylpiperidinium methylcarbonate.

Preferably, the 1-adamantyltrimethylammonium methylcarbonate or N,N-dimethyl-3,5-dimethylpiperidinium methylcarbonate is further reacted with calcium hydroxide in the presence of water to produce 1-adamantyltrimethylammonium hydroxide or N,N-dimethyl-3,5-dimethylpiperidinium hydroxide. In addition to water, the reaction may be performed in the presence of other solvents, such as alcohols, but additional solvents are not required. At least one mole equivalent of water is utilized in comparison to the 1-adamantyltrimethylammonium methylcarbonate or N,N-dimethyl-3,5-dimethylpiperidinium methylcarbonate, but preferably an excess of water is used. A molar excess of calcium hydroxide to 1-adamantyltrimethylammonium methylcarbonate or N, N-dimethyl-3,5-dimethylpiperidinium methylcarbonate is preferred, more preferably the molar ratio of calcium hydroxide: 1-adamantyltrimethylammonium methylcarbonate or N,N-dimethyl-3,5-dimethylpiperidinium methylcarbonate is in the range of 1.05 to 1.75.

Preferably, the reaction mixture of calcium hydroxide and 1-adamantyltrimethylammonium methylcarbonate (or N,N-dimethyl-3,5-dimethylpiperidinium methylcarbonate) is heated at an elevated temperature, preferably at reflux. The methanol produced is slowly distilled off until the vapor temperature is constant.

The 1-adamantyltrimethylammonium methylcarbonate or N,N-dimethyl-3,5-dimethylpiperidinium methylcarbonate itself may also be used as a templating agent for the production of zeolites, but it is preferably to utilize the 1-adamantyltrimethylammonium hydroxide or N, N-dimethyl-3,5-dimethylpiperidinium hydroxide. Zeolite synthesis is well-known in the art, and generally consists of reacting a silicon source, an aluminum source, (plus other metal sources if desired), and the templating agent at a temperature and for a time sufficient to form a molecular sieve. Typical silicon sources include colloidal silica, fumed silica, silicon alkoxides, and mixtures thereof. Typical aluminum sources include sodium aluminate, aluminum hydroxide, aluminum isopropoxide, aluminum sulfate, and aluminum nitrate.

The zeolite synthesis is typically performed in the presence of water. Other solvents such as alcohols may also be present. After the reaction mixture is formed, it is reacted at a temperature and a time sufficient to form a molecular sieve. Typically, the reaction mixture is heated at a temperature of about 100° C. to about 250° C. for a period greater than about 0.25 hours (preferably less than about 96 hours) in a sealed vessel under autogenous pressure. The reaction may be carried out in a batch, continuous, or semi-continuous manner using any appropriate type of reaction vessel or apparatus such as a stirred vessel or CSTR reactor. After the reaction is complete, the zeolite is recovered.

As synthesized, the zeolite will contain some of the templating agent in the pores. Any suitable method to remove the templating agent may be employed. The template removal is typically performed by a high temperature heating in the presence of an oxygen-containing gas, such as air or a mixture of oxygen and an inert gas. Preferably, the zeolite is heated at temperatures greater than 250° C. to remove the templating agent. Temperatures of from about 275° C. to about 800° C. are preferred.

The following examples merely illustrate the invention. Those skilled in the art will recognize many variations that are within the spirit of the invention and scope of the claims.

Example 1

1-Adamantyltrimethylammonium Hydroxide Preparation

Adamantyltrimethylammonium Methylcarbonate Synthesis:

1-Adamantamine (37.7 g, 0.25 mol), dimethylcarbonate (300 mL, 3.5 mol) and water (9 mL, 0.5 mol) are combined in an autoclave and heated to 150° C. for 10 hours. The autoclave is fitted with a pressure release so that the maximum pressure attained is 10 bar (1000 kPa). On cooling, the contents of the vessel are stripped completely dry and the residue slurried with 150 mL of acetone and cooled, filtered and washed with a little cold acetone. Drying gives a yield of 54 g (80.6%) H-NMR analysis is consistent with the structure.

1-Adamantyltrimethylammonium Hydroxide Synthesis:

Adamantyltrimethylammonium methylcarbonate (383 g, 1.42 mol) is added to water (1000 mL), followed by addition of calcium hydroxide (148 g, 2.0 mol). This addition is exothermic. The reaction mixture is then heated to reflux and the methanol produced is slowly distilled off until the vapor temperature is constant. The reaction mixture is then cooled slowly to 10° C. and the precipitated calcium carbonate and excess calcium hydroxide are filtered off on a Nutsche filter. The filter cake is washed with water (200 mL) and both the mother and wash filtrates are combined. The 1-adamantyltrimethylammonium hydroxide product yield is 1284 grams of solution with assay 20.2% w/w.

Example 2

1-Adamantyltrimethylammonium Hydroxide Preparation

1-Adamantamine (30.2 g, 0.2 mol), dimethylcarbonate (250 mL), methanol (25 mL), and water (4.5 g, 0.25 mol) are combined in an autoclave and heated at 140° C. for 8 hours. The vessel is cooled and the contents stripped to dryness. Crude yield is 51 g (94.6%). This crude 1-adamantyltrimethylammonium methylcarbonate material is used directly in the next step.

The crude methylcarbonate salt from the previous reaction is dissolved in 150 mL of deionized water, and a small amount of solid is filtered off and washed with a further 25 mL of deionized water. The filtrate is then transferred to a flask set up for distillation, and 21 g of calcium hydroxide is added. The mixture is heated to boiling and methanol and a small amount of steam and volatile organic material is distilled out. On cooling, the insoluble calcium salts are filtered off and washed with a little deionized water. The 1-adamantyltrimethylammonium hydroxide solution product yield is 204 g with an assay of 16.0% (77% overall).

Example 3

N,N-Dimethyl-3,5-Dimethylpiperidinium Methocarbonate Preparation 3,5-Dimethylpiperidine (28.2 g, 0.25 mol), dimethylcarbonate (300 mL), and water (9 g, 0.5 mol) are combined in an autoclave and heated to 150° C. for 6 hours. The autoclave is fitted with a pressure release so that the max pressure attained is 6 bar (600 kPa). The contents of the vessel are stripped to dryness, then 150 mL of acetone is added the mixture, stirred at 10° C., and then filtered to give the desired N,N-dimethyl-3,5-dimethylpiperidinium methylcarbonate salt (38 g, 70%). H-NMR analysis is consistent with the structure. This material may be converted to the hydroxide salt with calcium hydroxide as described in Example 1.

Although the method of the invention successfully produces 1-adamantyltrimethyl-ammonium methylcarbonate and N,N-dimethyl-3,5-dimethylpiperidinium methylcarbonate, the method is surprisingly less successful when applied to primary monoalkyl amines such as n-dodecylamine or benzylamine, giving a variety of byproducts and only low yields of the desired quaternary methylcarbonate salts.

I claim:

1. A method for preparing 1-adamantyltrimethylammonium methylcarbonate, comprising reacting 1-adamantylamine compound and dimethyl carbonate in the presence of water in a sealed vessel at a temperature of from 80 to 200° C., wherein the 1-adamantylamine compound is selected from the group consisting of 1-adamantylamine, 1-adamantylmethylamine, and mixtures thereof.

2. The method of claim 1 wherein the molar ratio of dimethyl carbonate: the 1-adamantylamine compound is in the range of 5 to 20.

3. The method of claim 1 wherein the molar ratio of dimethyl carbonate: the 1-adamantylamine compound is in the range of 8 to 14.

4. The method of claim 1 wherein the molar ratio of water:the 1-adamantylamine compound is in the range of 1 to 4.

5. The method of claim 1 wherein the reaction of the 1-adamantylamine compound with dimethyl carbonate is performed at a temperature in the range of 120-160° C.

6. The method of claim 1 wherein the 1-adamantylamine compound is 1-adamantylamine.

7. The method of claim 1 further comprising reacting the 1-adamantyltrimethylammonium methylcarbonate with calcium hydroxide in the presence of a water to produce 1-adamantyltrimethylammonium hydroxide.

8. The method of claim 7 wherein the molar ratio of calcium hydroxide: 1-adamantyltrimethylammonium methylcarbonate is in the range of 1.05 to 1.75.

9. The method of claim 7 wherein the reaction of 1-adamantyltrimethylammonium methylcarbonate with calcium hydroxide in the presence of water is performed at reflux.

* * * * *